(12) United States Patent
Bonne et al.

(10) Patent No.: US 6,838,287 B2
(45) Date of Patent: Jan. 4, 2005

(54) FLUID MIXTURE COMPOSITION SENSOR

(75) Inventors: Ulrich Bonne, Hopkins, MN (US); Kenneth Creasy, Budd Lake, NJ (US); Troy W. Francisco, Williamsville, NY (US)

(73) Assignee: Honeywell International Inc., Morristown, NJ (US)

( * ) Notice: Subject to any disclaimer, the term of this patent is extended or adjusted under 35 U.S.C. 154(b) by 297 days.

(21) Appl. No.: 10/027,039

(22) Filed: Dec. 20, 2001

(65) Prior Publication Data

US 2003/0119197 A1 Jun. 26, 2003

(51) Int. Cl.[7] .................. G01N 27/00; G01N 25/08; G01N 27/416; G01N 33/48; G01N 21/00
(52) U.S. Cl. ................. 436/149; 422/68.1; 422/83; 422/50; 422/78; 422/94; 422/95; 422/96; 422/97; 422/98; 436/43; 436/147; 436/150; 436/151; 436/149; 436/155; 73/1.01; 73/1.02
(58) Field of Search .................. 422/68.1, 83, 50, 422/78, 94–98; 436/43, 147, 149, 150, 151, 155; 73/1.01, 1.02

(56) References Cited

U.S. PATENT DOCUMENTS

| | | | | | |
|---|---|---|---|---|---|
| 4,478,076 | A | * | 10/1984 | Bohrer | 73/204.16 |
| 4,501,144 | A | * | 2/1985 | Higashi et al. | 73/204.26 |
| 4,944,035 | A | * | 7/1990 | Aagardl et al. | 702/136 |
| 5,515,714 | A | | 5/1996 | Sultan et al. | |
| 6,019,505 | A | * | 2/2000 | Bonne et al. | 374/40 |
| 6,169,965 | B1 | | 1/2001 | Kubisiak et al. | |
| 6,361,206 | B1 | | 3/2002 | Bonne | |

FOREIGN PATENT DOCUMENTS

| | | |
|---|---|---|
| EP | 0724151 A1 | 7/1996 |
| EP | 0871029 A2 | 10/1998 |

OTHER PUBLICATIONS

R.Higashi, R.G. Johnson, AK Mathur, AN Pearman and U Bonne Microstructure Sensors for Flow Differential Pressure and Energy Measurement, IGT Symposium on Natural Gas Energy Measurement, Chicago, IL., Apr. 30–May 2, 1986.

U.Bonne "Fully C9ompensated Flow Microsensor for Electronic Gas Metering", Intl. Gas Research Conference, Orlando, FL, Nov. 16–19, 1992, Proceedings, vol. III p. 859.

U.Bonne, "Sensing Fuel Properties with Thermalmicrosensors", SPIE Smart Electronics and MEMS Conference, San Diego, CA, Feb. 25–29, 1996, Paper No. 2722–24.

U.Bonne and D.Kubisiak, Genetron Gas Conconcentration Sensor, Cat. No. SEN–R00–001, HIL–Plymouth, Sep. 28, 2000.

U.Bonne, K.Creasy, T.Francisco and D.Kubisiak "Rugged Microsensor for Process Stream Composition Monitoring" 15th International Forum on Process Analysis & Control (IFPAC), Amelia Island, Florida Jan. 21–24, 2001.

U.Bonne and D.Kubisiak, "Actuation–Based Microsensors", Journal of Smart Materials and Structures (IoP), Special Issue on "Space Applications for MEMS", Submitted Feb. 2000 in Print.

* cited by examiner

Primary Examiner—Yelene Galeh
Assistant Examiner—Brian Sines
(74) Attorney, Agent, or Firm—Kris T. Fredrick

(57) ABSTRACT

An improved, affordable, and rapid fluid mixture composition or process monitor based on a thermal microstructure sensor. This is preferably accomplished with a microbridge sensor design that has reduced susceptibility to interfering components of the mixture. The sensor described herein is therefore suitable for monitoring the concentration of at least one component in a fluid mixture when the fluid mixture consists of either (1) two components with very different thermal conductivities; or (2) three or more components wherein at least one component has a very different thermal conductivity and the effects of the other components can be largely eliminated, especially if the component of interest is hydrogen and the interference is from the variability in the concentrations of $CO_2$ and $H_2O$.

28 Claims, 8 Drawing Sheets

FLUID MIXTURE COMPOSITION SENSOR

BACKGROUND OF THE INVENTION

Compositional monitoring of fluid streams (gas or liquids) is critical for optimal control of industrial processes. Available monitors (analytical instruments) require costly maintenance and sampling to perform this function. To achieve greater process yields, competitive cost reductions, and increased product quality, more reliable and lower cost analytical instruments, monitors or preferably rugged and compact sensors, to better achieve above control objectives, are needed.

One example of a fluid stream process control objective is the blending of two individual refrigerants to achieve a set composition of a gaseous or liquid mixture of such refrigerants. Rugged, affordable, wide range, low power, and stable sensors are needed to enable measurement of small changes in the composition of such mixtures, or of small deviations in the set point of the concentration of one component of such a binary mixture.

Another example of a fluid stream can be found in a Proton Exchange Membrane fuel cell (PEMFC), which uses an electrochemical process to combine hydrogen and oxygen into water, producing electric current in the process. First, the combustible nature of hydrogen makes its detection and sensing vitally important from a safety point of view, in the air outside a PEMFC. Second, and of more relevance to the present invention, because hydrogen is the key fuel in a PEM fuel cell, the monitoring and control of the $H_2$ concentration is needed for proper operation of a PEMFC. The need therefore also exists for a reliable and low-cost fluid mixture composition sensor for process monitoring and control in and emissions detection around PEMFCs.

In recent years, due to the advance of silicon semiconductor technology, much attention has been focussed on the use of a Pd metal-oxide-semiconductor (MOS) structure as a semiconductor hydrogen sensor. Pd metal has been used in hydrogen sensors because it has a good catalytic activity and can dissociate the hydrogen molecule absorbed to the surface into hydrogen atoms. A portion of the hydrogen atoms diffuses through the Pd metal and absorbes to the interface between the metal and the oxide layer. These hydrogen atoms, after polarization, cause a change in the Schottky barrier height between the oxide layer and the silicon semiconductor and thus the electrical properties of the device. In the early days, I. Lundstrom proposed a $Pd/SiO_2/Si$ MOS field effect transistor structure with a Pd gate [Lundstrom, M. S. Shivaraman, and C. Svensson, J. Appl. Phys. 46, 3876 (1975)]. After the hydrogen is absorbed to the Pd gate, the altered threshold voltage and terminal capacitance are used as the bases for the detection of hydrogen.

Another technique to sense hydrogen is to measure changes in the electrical resistivity of a Pd thin film [P. A. Michaels, Design, Development, and Prototype Fabrication of an Area Hydrogen Detector, Bendix Corporation, Southfield, Mi., 1964, Contract NAS8-5282]. A thin film is deposited on a substrate, usually in the form of two resistors in a Wheatstone bridge. An essentially inert, electrically insulating, hydrogen impermeable passivation layer covers at least one of the resistors, and the other resistor is left uncovered. The difference in electrical resistances of the covered resistor and the uncovered resistor is related to the hydrogen concentration in a fluid to which the sensor element is exposed.

The most popular (but not solely sensitive to) hydrogen sensor is the "catalytic combustible" or "hot wire" sensor. These sensors utilize as the detector element a Group VIIIB metal element (Ni, Pd, Pt) that is heated to catalytically oxidize the hydrogen, with the resulting change in temperature and associated resistance of the "hot wire or bead" being the measured parameter for the determination of the presence of hydrogen.

Although all of the above methods may be used to sense hydrogen in a gaseous mixture, they all are subject to specific limitations. All of the sensors described above are subject to small impurities that can cause uncontrolled drift, making the sensor unusable. Likewise, each of these sensors may be poisoned by trace quantities of $SO_x$. Furthermore, the MOS semiconductor and catalytic combustible hydrogen sensors require $O_2$ to operate. In $O_2$ deficient environments or above the upper explosive limit, the oxidation process is quenched. This causes the hot element of the catalytic combustible sensor to heat less or not at all, causing the sensor to generate erroneous readings.

A number of approaches have been devised to measure the thermal conductivity (TC), of a fluid of interest. A traditional approach for the TC measurement has been via calorimetry using reversible step increases of energy fed to a thermally isolated or adiabatic system.

Further to the measurement of thermal conductivity, as will be discussed in greater detail below, very small, low power and affordable "microbridge" semiconductor chip sensors have been used in which etched semiconductor "microbridges" are used as heaters and sensors. The structure of such sensors might be similar to that of thermally isolated thin "hot-film" microanemometers for measuring flow rates. Semiconductor chip sensors of the class described above are treated in a more detailed manner in U.S. Pat. Nos. 4,478,076, 4,478,077, 4,501,144, 4,651,564, and 4,683,159, all of common assignee with the present invention.

A thermal conductivity based sensing approach that takes advantage of the very high thermal conductivity of hydrogen is stable and impervious to poisoning, but does suffer from interference by large changes in $H_2O$ and $CO_2$.

The ability to make accurate measurements of the concentration of components in a mixture via thermal conductivity is generally dependent on the temperature at which such measurements are made, because each component has a different temperature dependence of thermal conductivity. The present invention, as discussed below, selects a measurement temperature at which the components differ the most in their respective values of thermal conductivity, within the limits imposed by heeding low-power, fluid stability and safety criteria.

It is therefore an object of the present invention to provide an improved fluid mixture composition sensor, using a microbridge structure, able to overcome the aforementioned deficiencies of the prior art fluid mixture detectors. More specifically, one object of the present invention is to provide an improved method of operating thermal conductivity sensors that results in: a hydrogen concentration measurement with reduced susceptibility to $H_2O$ and/or $CO_2$; a more accurate component concentration measurement in fluid mixtures in general.

Other objects and advantages of the present invention will be more fully apparent from the ensuing disclosure and appended claims.

SUMMARY OF THE INVENTION

The present invention overcomes many of the disadvantages associated with the prior art by providing an in-situ, affordable and rapid process monitor or fluid composition sensor based on a thermal microstructure sensor.

DETAILED DESCRIPTION OF THE INVENTION

The present invention is directed to a sensor that incorporates an in-situ, low-cost process monitor, and other advanced features to accurately monitor the composition of fluid streams. The preferred embodiment of the sensor is comprised of a microbridge sensor which is suitable for accurate hydrogen sensing.

The mircosensor system or "microbridge," as it will be referred to herein, though not limiting, is presently preferred for several reasons. The system is fast reacting, is accurate, and sensitive because of its advantageous coupling to the fluid of interest and small and adaptable to a variety of configurations.

The microbridge semiconductor chip sensor contemplated, for example, in certain embodiments preferred for the invention may resemble the form of one or more of the microbridge systems illustrated in the patents identified above. Such a system is exemplified by FIGS. 1–3 taken from U.S. Pat. No. 4,994,035 to Aagard et al. A discussion of that example will now be presented, as it will be helpful in understanding the present invention. While the present discussion is believed sufficient, to the extent necessary, any additional material contained in the microbridge related patens cited is deemed to be incorporated herein by reference.

Figure 1:
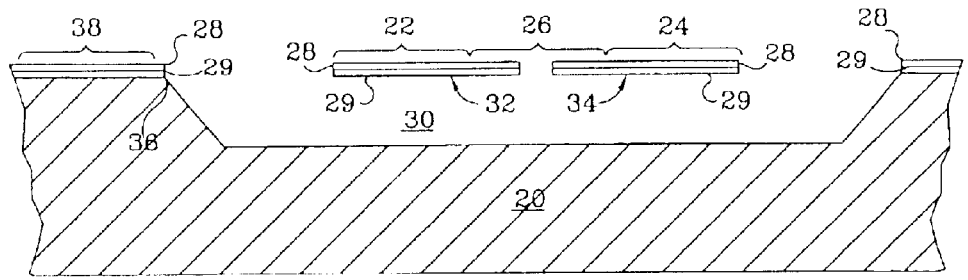
FIGS. 1–3 are different views of a prior art embodiment of a microbridge flow sensor.
Figure 2:
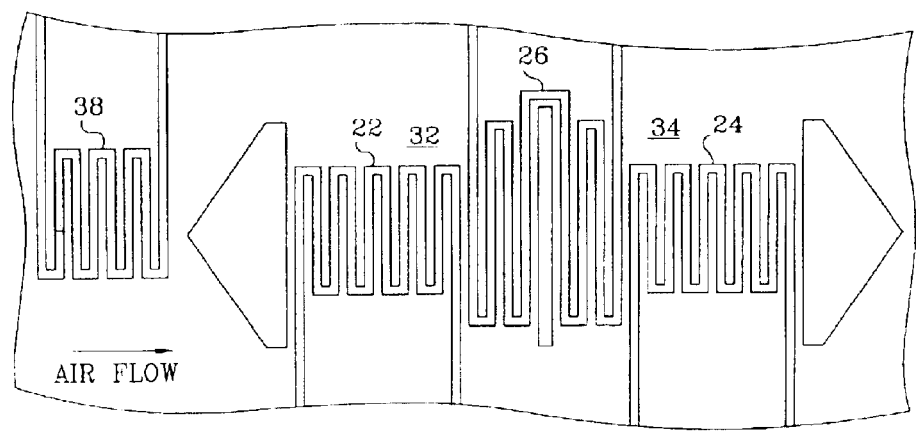
Figure 3:
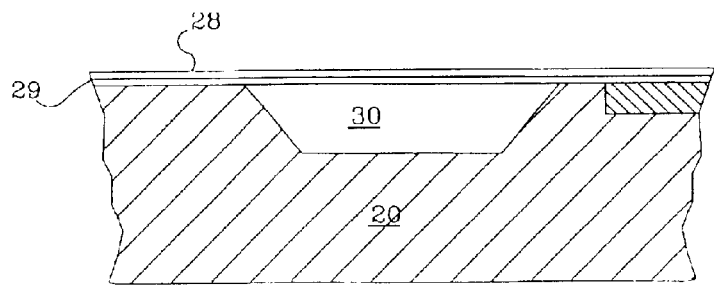

The prior art system of FIGS. 1–3 contemplates a pair of thin film temperature sensors 22 and 24, a thin film heater 26 and a support member 20 supporting the sensors and heater out of contact with the base substrate. Sensors 22 and 24 are disposed on opposite sides of heater 26. Support member 20 is a semiconductor, preferably silicon, chosen because of its adaptability to precision etching techniques and ease of electronic chip producibility. The embodiment may include one or two identical temperature sensing resistor grids 22 and 24 acting as a thin film heat sensor and a centrally located heater resistor grid 26 acting as the thin film heater.

Sensors 22 and 24 and heater 26 may be fabricated of any suitable, stable metal or alloy film. The metal used may be a nickel-iron alloy sometimes referred to as permalloy, with a composition of 80 percent nickel and 20 percent iron. The sensor and heater grids are encapsulated in a thin film of dielectric, typically comprising layers 28 and 29 and preferably silicon nitride, $Si_3N_4$ to form the film members. In the preferred embodiment, heater 26 has a normal operating range of 10 to 200 degrees Celsius above the ambient temperature, which is related to the power supplied to the thin film Pt serpentine heater element.

In the FIGS. 1 and 2, the sensor comprises two thin film members 32 and 34, with member 32 comprising sensor 22 and member 34 comprising sensor 24, each member comprising one-half of the heater 26 and having a preferred dimension of 150 microns wide and 400 microns long.

The system further describes an accurately defined fluid space 30 that effective surrounds elements 22, 24, 26, and is achieved by fabricating the structure on silicon surface 36. Thin film elements 22, 24, and 26 have thicknesses of approximately 0.08 to 0.12 microns with line widths on the order to 5 microns and spaces between lines on the order of 5 microns. The elements encapsulated in the silicon nitride film preferably have a total thickness of approximately 0.8 microns or less. The fluid space 30 may be fabricated by subsequently etching an accurately defined fluid space of about 100 microns deep into silicon body 20 beneath members 32 and 34.

Members 32 and 34 connect to top surface 36 of semiconductor body 20 at one or more edges of depression or fluid space 30. As illustrated in FIG. 3, members 32 and 34 may be bridged across depression 30; alternately, for example, members 32 and 34 could be cantilevered over depression 30.

In the microbridge system shown, heat flows from the heater to the sensor by means of both solid and fluid couplings therebetween. Of note is the fact that silicon nitride ($Si_3N_4$), besides being a good electrical insulator, is also an effective solid thermal insulator. Because the connecting silicon nitride film within members 32 and 34 is a good insulator, heat transmission through the solid does not dominate the propagation of heat from heater 26. This further enhances the relative amount of the heat conducted to sensing resistors 22 and 24 from heater resistor 26 by flow through the surrounding fluid rather than through the supporting nitride film. Moreover, the supporting silicon nitride film has a low enough thermal conductivity that sensing resistor grids 22 and 24 can be located immediately adjacent or juxtaposed to heating resistor grid 26. Thus, sensing resistor grids 22 and 24 are in effect suspended rigidly in the fluid space proximate heater resistor 26 and act as thermal probes to measure the temperature of the air near and in the plane of heater resistor grid 26.

Figure 4:
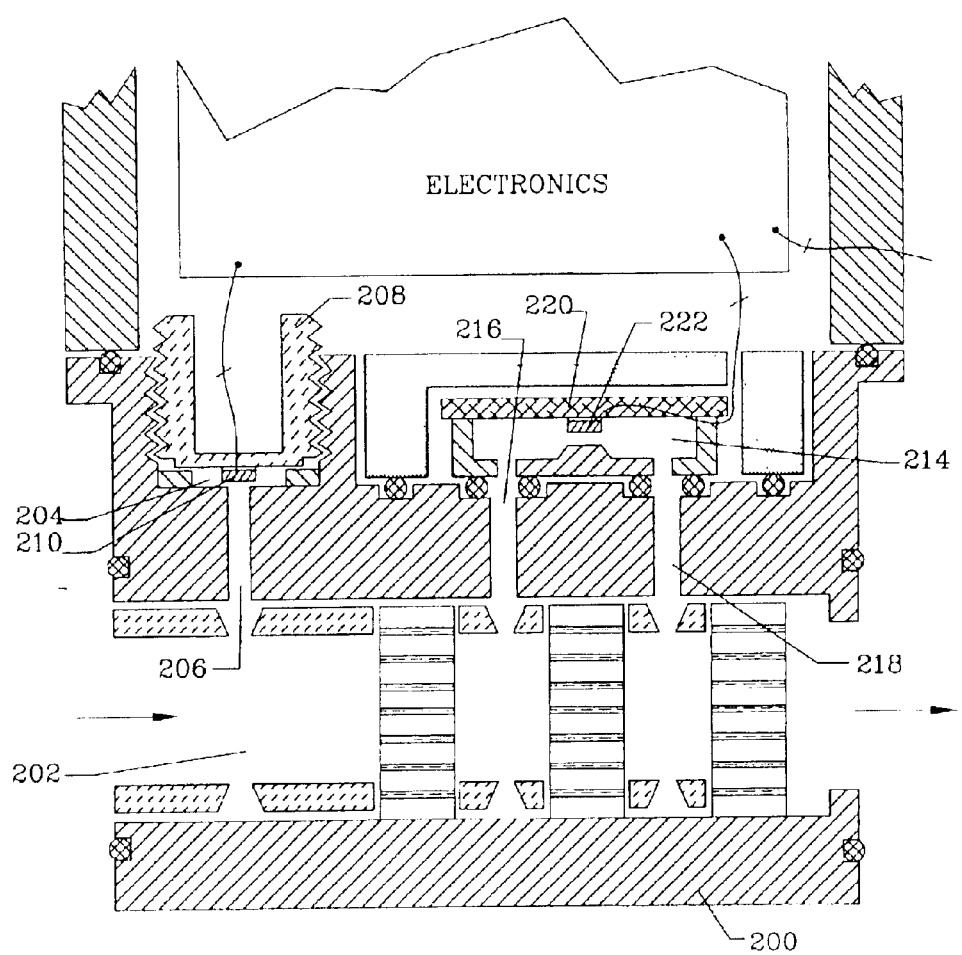
FIG. 4 is a partial cut-away view of a microbridge sensor package in a fluid environment.

FIG. 4 is a partial cut-away view of a microbridge sensor package placed in line with a flow pipe. A main flow channel 200 having a central bore 202 is connected to the pipe that carries a fluid of interest. A first chamber 204 is in fluid communication with the central lumen 202 of the main flow channel 200 via a single bore 206. A header 208 having a first microbridge sensor 210 mounted thereto is inserted into the first chamber 204 and secured to the main flow channel 200 as shown. In this configuration, the first microbridge sensor is exposed to the fluid of interest with substantially zero flow. The first microbridge sensor 210 is typically used to measure fluid properties such as thermal conductivity, thermal diffusivity, specific heat, temperature, and pressure.

Figure 5:
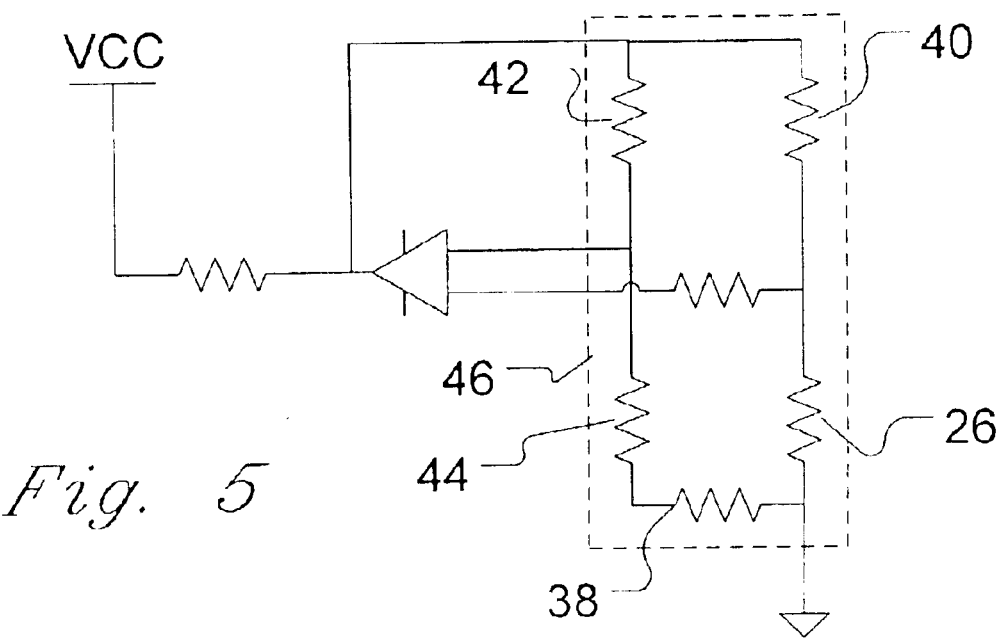
FIG. 5 is the heater control circuit of the present invention.

The operation of the system in sensing thermal conductivity is discussed briefly with reference to FIG. 5. The heater control circuit illustrated in FIG. 5 uses a Wheatstone bridge 46 to maintain heater 26 at a predetermined temperature rise above ambient as controlled by heat sunk reference resistor 38. Wheatstone bridge (WB) 46 is shown comprising heater resistor 26 and a resistor 40 in its first leg and a resistor 42, heat sunk resistor 38 with resistor 44 in its second leg. Resistor 44, which is not dependent upon temperature, is adjusted initially so that the sensor output (i.e. the heater voltage or the top WB voltage) for a reference fluid of known TC varies minimally with ambient temperature, and outputs an approximately constant value of TC at a predetermined reference temperature value. Remaining TC output variabilities are shown, by way of example, in FIG. 11.

Figures 6, 7:
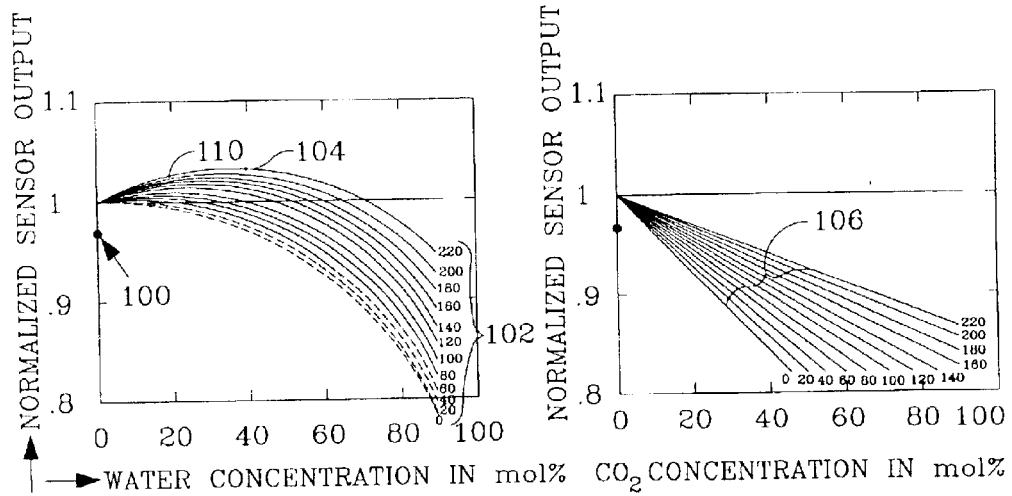
FIGS. 6–10 are graphical representations of the sensor output versus various fluid compositions.

FIG. 6 is a graphical representation of the normalized microbridge sensor output or thermal conductivity (TC) of a sensed fluid containing a known hydrogen concentration as a function of the water vapor concentration in a $N_2+H_2O$ fluid stream. The point represented by reference numeral 100 is the sensor output or TC where the hydrogen concentration is at zero percent of the sensed fluid. Multiple plots 102 of sensor output or TC versus water vapor concentration are shown for temperature values ranging from 0 to 220 degrees Celsius. As shown in FIG. 6, the introduction of $H_2O$ at low concentrations causes the TC to increase. Eventually, as the concentration of $H_2O$ is further increased at any fluid temperature, the sensor output or TC reaches a maximum value and eventually decreases. This behavior can be explained as being due to the formation of dimers and trimers of $H_2O$, which have a larger molecular weight and lower TC than a gas of individual molecules of $H_2O$. The lines represented by dashes in FIG. 6 are theoretical values since water vapor condenses at low temperatures. The point on the top curve indicated by reference numeral 104 indicates that at about the 40 mole-percent concentration of $H_2O$, the normalized sensor output is about double that found at one percent hydrogen concentration.

FIG. 7 is another graphical representation of normalized sensor output or TC as a function of $CO_2$ concentration in a fluid stream comprising $N_2+CO_2$. In comparison to FIG. 6, the lines representing the thermal conductivity 106 are more linear, which is due to the $H_2O$ molecule being a polar or non-symmetrical molecule, while $CO_2$ is a nonpolar or symmetrical molecule. Further, the plots 106 in FIG. 2 are continuously decreasing, never increasing. The present invention proposes to use this non-linear $H_2O$ effect on the TC of a fluid stream to minimize the interference generated by $H_2O$ and $CO_2$.

Figure 8:
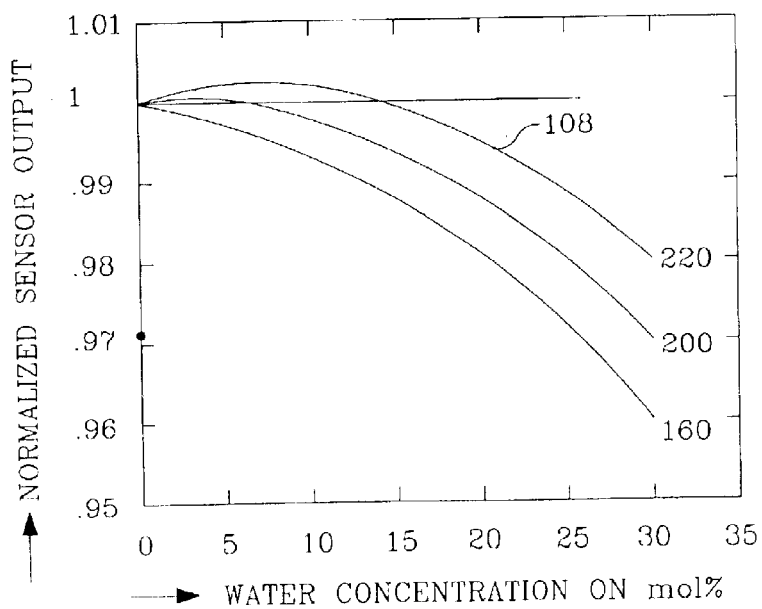

In FIG. 8, the normalized sensor output or TC is shown for a fluid where the $CO_2$ concentration is equal to the $H_2O$ concentration. This plot reflects a combination of the plots in FIGS. 6 and 7. Evidence of this can be found, for example, at 20 mole-percent concentration of $H_2O$ and $CO_2$, and a temperature of 220 degrees Celsius. At these characteristics, represented by reference numeral 108, the sensor output or TC is less than the sensor output or TC at a zero mole-percent $H_2O$ and $CO_2$ concentration value. In FIG. 6, the sensor output or TC represented by reference numeral 110, is greater than the sensor output of TC at a zero mole-percent $H_2O$ concentration.

Figure 9:
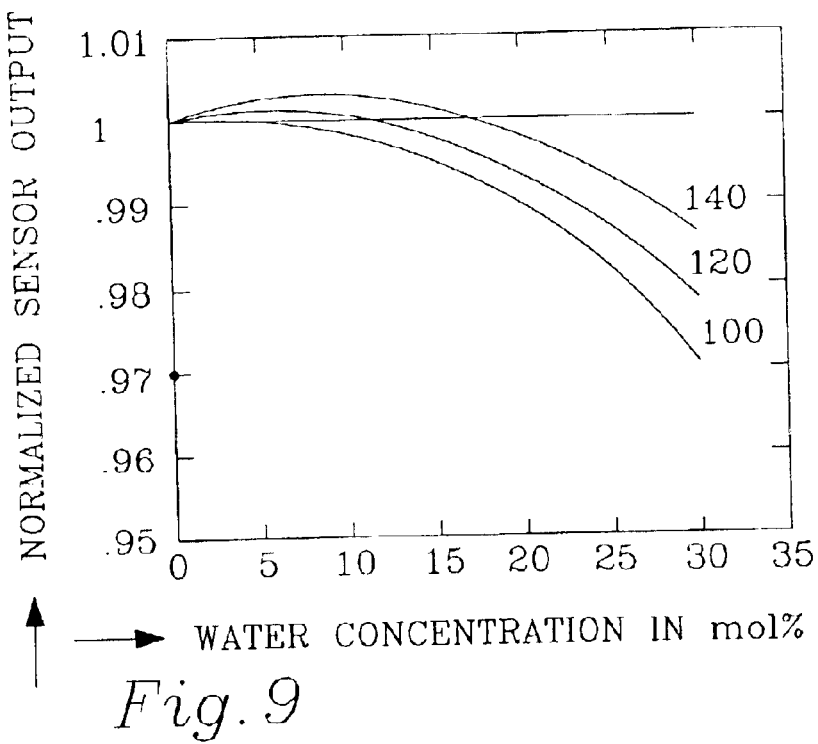
Figure 10:
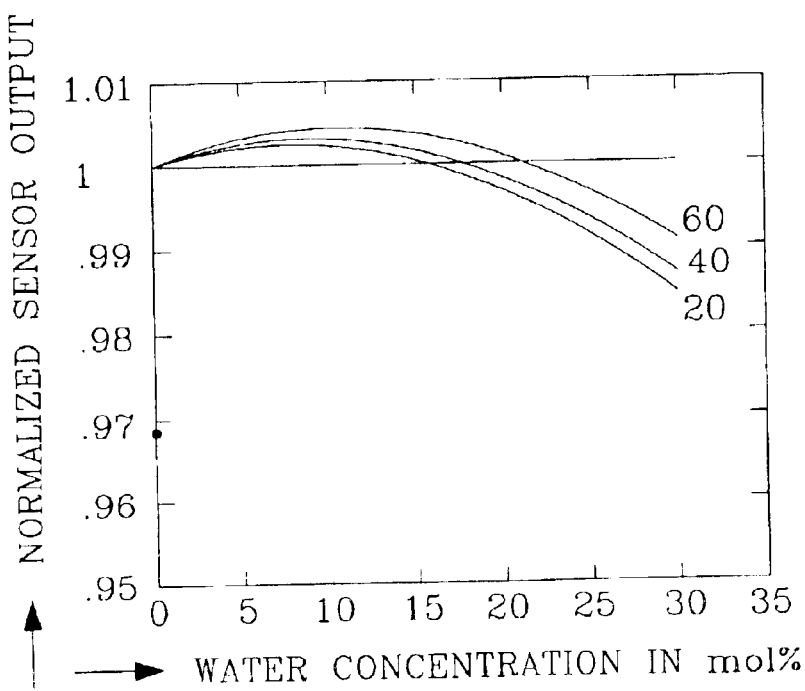

FIGS. 9 and 10 are further extensions of this concept. Specifically, in FIG. 9, a graphical representation of the normalized sensor output or TC is shown as a function of $H_2O$ concentration in the fluid stream, where the $CO_2$ is three times greater than the concentration of $H_2O$. In FIG. 10, the concentration of $CO_2$ is held constant at 400 ppm, and the $H_2O$ concentration is allowed to vary.

The present invention, therefore, also takes advantage of the non-linear $H_2O$ TC effect by allowing the optimal heater environment temperature to vary. By adjusting the heater temperature to a level such that the average temperature in the micro-environment around the heater is suggested by the most linear TC plot shown in FIGS. 8–10, the effects of $H_2O$ and $CO_2$ can be significantly reduced. This is made with the assumption that the approximate ratio of $H_2O/CO_2$ is known and is relatively constant in a particular application, such as a PEMFC fuel cell or refrigerant fluid stream.

More specifically, a determination is first made of the variability range of $CO_2$ and $H_2O$ in the specific sensing application. As indicated above, a determination is made of the optimal measurement temperature for minimum interference of the aforementioned variability. This determination may be made in the factory using a look up table, graph, other low cost devices, or the like. After the optimal measurement temperature is determined, the heater 26 temperature is set to approximately 150 percent of the optimal temperature desired to allow for the temperature gradient around the heater 26. In most sensing applications, the heater temperature will be set at varying optimal temperatures depending on the concentration of $CO_2$ and $H_2O$ in the sensed fluid. Alternate embodiments of the present invention may involve the ability to reset the optimal measurement temperature in the field should the composition of the sensed fluid change or other need arise.

In the preferred embodiment, this requires adjusting the heater temperature from approximately 210 degrees for the fluid stream composition in FIG. 8 to approximately 130 degrees Celsius for the fluid stream composition in FIG. 9. In FIG. 10, the optimal or preferred sensor heater environment temperature is shown to be near 40 degrees Celsius, or as low as possible. In a safety application in room air, $CO_2$ is approximately 300–600 ppm, $H_2O$ is approximately 1–3 mole-percent, and the heater temperature is approximately 40 degrees Celsius. In a PEMFC fuel cell application with a high water vapor concentration, $CO_2$ is approximately 10 mole-percent, $H_2O$ is approximately 30 mole-percent, and the preferred heater temperature is approximately 120 degrees Celsius.

Figure 11:
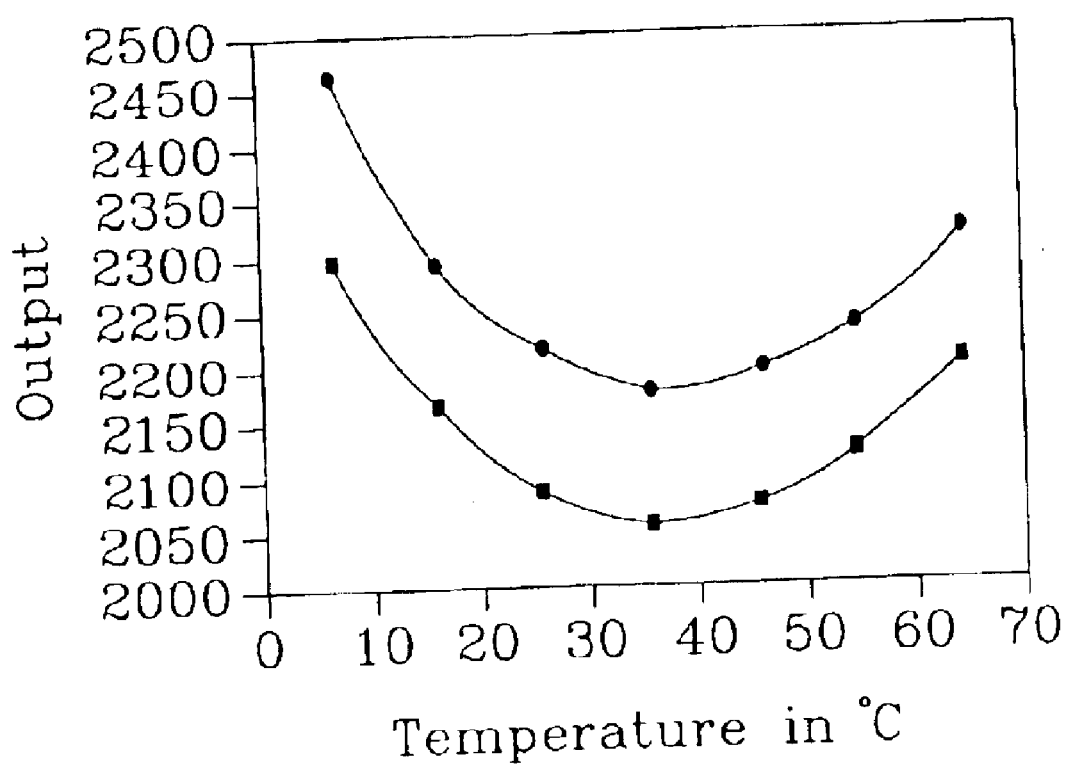
FIG. 11 is a graphical representation of sensor output verses temperature for two levels of Hydrogen concentration before final temperature compensation.
Figure 12:
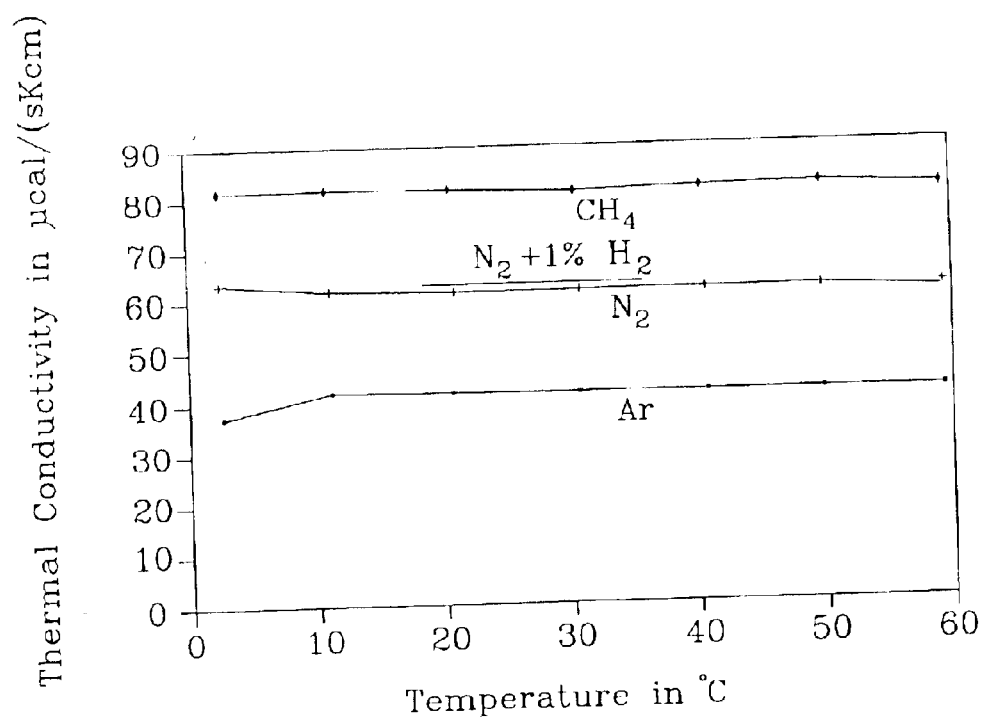
FIG. 12 is a graphical representation of sensor output versus temperature for various fluid concentrations in accordance with the present invention, after temperature compensation.
Figure 13:
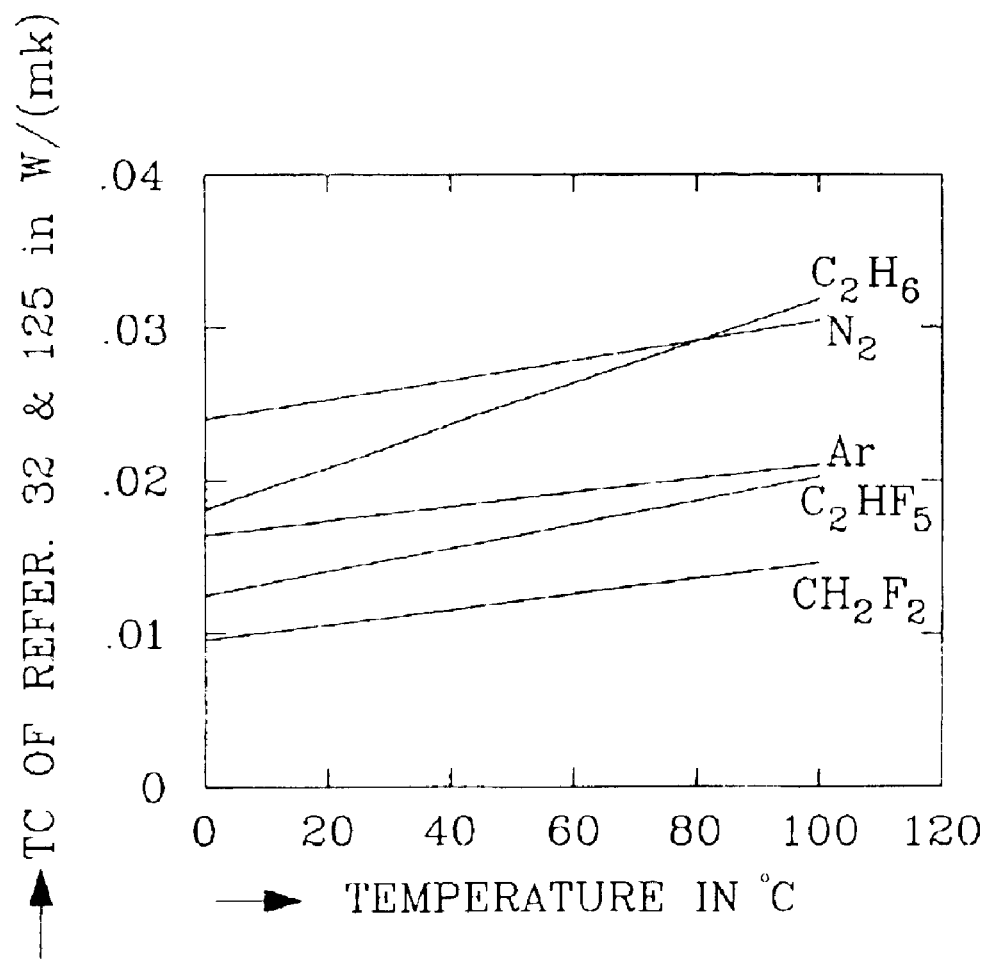
FIG. 13 is a graphical representation of sensor output versus temperature for various fluid concentrations in accordance with the present invention, before temperature compensation.

The fluid sensor output, without the temperature compensation method of the present invention, as depicted in FIG. 11, is shown as a function of the temperature for $H_2$ concentration at both zero mole-percent and at one mole-percent. Likewise, FIG. 13 is a representation of the sensor output for various other fluid compositions over temperature, before temperature compensation. FIG. 12 is the same graphical representation as FIG. 13 using the temperature compensation invention described herein.

The TC based sensor described herein is therefore suitable for monitoring the composition of at least one element in a fluid mixture when the fluid mixture is (1) two components with very different thermal conductivities; or (2) three or more components wherein at least one component has a very different TC and the effects of the other components can be largely eliminated.

Having thus described the preferred embodiments of the present invention, those of skill in the art will readily appreciate that the teachings found herein may be applied to yet other embodiments within the scope of the claims hereto attached.

What is claimed is:

1. A method for obtaining a measure of the thermal conductivity of a first component of a fluid of interest that include the first component and two or more other components using a thermal conductivity sensor, the thermal conductivity sensor having a heater and a temperature sensor, wherein each of said heater and said temperature sensor are in thermal communication with the fluid of interest, the method comprising the steps of:

determining the variability range of at least one of the two or more other components in the fluid of interest;

energizing the heater with an input signal to induce an elevated temperature condition in said heater, the elevated temperature condition being such that the combined thermal conductivity of the two or more other components is less variable with concentration of the two or more other components than the individual thermal conductivities of the two or more other components; and obtaining a measure of the thermal conductivity of the that component using said temperature sensor.

2. The method of claim 1 wherein at least one of the two or more other components includes $H_2O$ and at least one of the two or more other components includes $CO_2$, the method further comprising the steps of:

determining the variability range of $CO_2$ in the fluid of interest.

3. The method of claim 1 wherein at least one of the two or more other components includes $H_2O$ the method further comprising the step of selecting the elevated temperature condition for said heater by:

measuring the thermal conductivity of the fluid of interest over a range of temperatures; and selecting the elevated temperature based on the thermal conductivity measurements to reduce the effect of $H_2O$.

4. The method of claim 2 further comprising the step of selecting the elevated temperature condition for said heater by:

measuring the thermal conductivity of the fluid of interest over a range of temperatures; and selecting the elevated temperature based on the thermal conductivity measurements to reduce the combined effects of $H_2O$ and $CO_2$.

5. The method of claim 1 wherein the elevated temperature condition far said heater may be configured in the field.

6. A fluid sensor for determining a selected property of one or more components in a fluid of interest, comprising:

a heater;

a thermal sensor in proximate position to said heater and in thermal communication therewith through the fluid of interest, said sensor having a temperature dependent output;

measuring means for obtaining a measure of the selected property of at least one of the one or more components of the fluid of interest using said thermal sensor; and energizing means connected to said heater for energizing the heater to induce an elevated temperature condition in said thermal sensor, wherein said elevated temperature condition is selected to reduce the effect of at least one of the components in the fluid of interest on the selected property that is measured by the measuring means.

7. The fluid sensor of claim 6 wherein at least one of the one or more components includes $H_2O$ and at least another of the one or more components includes $CO_2$, and said elevated temperature condition is selected to reduce the effect of $H_2O$ and $CO_2$.

8. The fluid sensor of claim 6 wherein said fluid sensor is used to sense hydrogen concentration in the fluid of interest.

9. The fluid sensor of claim 6 wherein the fluid of interest includes a gas.

10. The fluid sensor of claim 9 wherein the output of the sensor is used to control the concentration of individual components resulting from mixing at least two components.

11. The fluid sensor of claim 6 wherein the fluid of interest includes a liquid.

12. The fluid sensor of claim 6 wherein the fluid of interest includes a refrigerant.

13. A method of compensating an output of a fluid sensor that includes a heater and a temperature sensor, comprising:

determining the range of $H_2O$ in the fluid to be sensed;

selecting a heater temperature to reduce the effect of $H_2O$ on the output of the fluid sensor; and heating the fluid to be sensed using the heater to the selected temperature value.

14. The method of claim 13 further comprising the steps of:

determining the range of $CO_2$ in the fluid to be sensed; and selecting the beater temperature value to reduce the effect of $CO_2$ on the fluid sensor.

15. The method of claim 13 wherein the selected temperature is chosen to reduce non-linear sensor resistance values caused by the $H_2O$ in the range of $H_2O$ concentration.

16. The method of claim 13 wherein the selected temperature is chosen to reduce non-linear sensor resistance values caused by the $CO_2$ in the range of $CO_2$ concentration.

17. A method for obtaining a measure of the thermal conductivity of a first component of a fluid of interest that include the first component, a second component and a third component using a thermal conductivity sensor, the thermal conductivity sensor having a heater and a temperature sensor, wherein each of said heater and said temperature sensor are in thermal communication with the fluid of interest, and wherein the second component of the fluid of interest includes polar or non-symmetrical molecules, and the third component of the fluid of interest includes non-polar or symmetrical molecules, the method comprising the steps of:

determining the variability range of the second component and/or the third component in the fluid of interest;

energizing the heater with an input signal to induce an elevated temperature condition in said heater, the elevated temperature condition being such that the combined thermal conductivity of the second component and the third component is less variable with concentration of the second component and the third component than the individual thermal conductivities of the second component and the third component; and obtaining a measure of the thermal conductivity of the first component using said temperature sensor.

18. The method of claim 17 wherein at least one of the first and second components includes $H_2O$, the method further comprising the step of selecting the elevated temperature condition for said heater by:

measuring the thermal conductivity of the fluid of interest over a range of temperatures; and selecting the elevated temperature based on the thermal conductivity measurements to reduce the effect of $H_2O$.

19. The method of claim 17 wherein the elevated temperature condition for said heater may be configured in the field.

20. A method for compensating an output of a fluid sensor that includes a heater and a temperature sensor, comprising:

determining the range of $H_2O$ and $CO_2$ in the fluid to be sensed;

energizing the heater in the fluid to be sensed to one or more temperatures and varying the amount of $H_2O$ and $CO_2$ in the fluid to be sensed while monitoring the output of the fluid sensor;

selecting a heater temperature value to reduce the effect of $H_2O$ and $CO_2$ on the output of the fluid sensor; and heating the fluid to be sensed using the heater to the selected temperature value.

21. A method for determining the thermal conductivity of a first component in a fluid stream, wherein the fluid stream includes the first component and two or more other components, each having a thermal conductivity, wherein an approximately relative concentration of the two or more other components is known, the method comprising the steps of:

exposing a thermal conductivity sensor to the fluid stream, wherein the thermal conductivity sensor includes a heater and a temperature sensor;

elevating the temperature of the heater to an elevated temperature where the combined thermal conductivity of the two or more other components is less variable with concentration of the two or more other components than the individual thermal conductivities of the two or more other components; and obtaining a measure of the thermal conductivity of the first component using the temperature sensor.

22. A method according to claim 21 wherein, at the elevated temperature, the combined thermal conductivity of the two or more other components is relatively constant over a range of concentrations of the two or more other components.

23. A method according to claim 21 wherein, at the elevated temperature, the combined thermal conductivity of the two or more other components does not substantially affect the measure of the thermal conductivity of the first component.

24. A method according to claim 23 wherein, at the elevated temperature, the thermal conductivities of the two or more other components substantially cancel each other out, so that the measure of the thermal conductivity of the first component can more easily be obtained.

25. A method according to claim 21 wherein the two or more other components include a second component and a third component.

26. A method according to claim 25 wherein the second component includes $H_2O$.

27. A method according to claim 26 wherein the second component includes $CO_2$.

28. A method for determining the thermal conductivity of a first component in a fluid stream, wherein the fluid stream includes the first component and two or more other components, each having a thermal conductivity, wherein an approximately relative concentration of the two or more other components is known, the method comprising the steps of:

exposing a thermal conductivity sensor to the fluid stream, wherein the thermal conductivity sensor includes a heater and a temperature sensor;

elevating the temperature of the beater to an elevated temperature;

obtaining a measure of the thermal conductivity of the first component using the temperature sensor; and wherein the elevated temperature is such that the thermal conductivities of the two or more other components substantially cancel each other out so that the measure of the thermal conductivity of the first component can more easily be obtained.

* * * * *